United States Patent [19]

Oscarsson

[11] 4,432,765
[45] Feb. 21, 1984

[54] ATTACHMENT DEVICE FOR MEDICAL FLUIDS BAG

[76] Inventor: Rolf A. Oscarsson, 10 Gemini Cir., Andover, Mass. 01810

[21] Appl. No.: 398,287

[22] Filed: Jul. 14, 1982

[51] Int. Cl.³ .............................................. A61M 5/00
[52] U.S. Cl. ...................................... 604/411; 222/83
[58] Field of Search ........ 604/201, 204, 244, 251–254, 604/411–415, 905, 272, 174; 285/3, 4, 307, 309–312; 222/81, 83, 83.5; 137/318; 141/19, 329, 330

[56] References Cited

U.S. PATENT DOCUMENTS

| | | | |
|---|---|---|---|
| 2,234,686 | 3/1941 | Walter | 604/174 |
| 3,139,343 | 6/1964 | Baselt | 222/83.5 X |
| 3,494,641 | 2/1970 | Caregnato | 285/311 |
| 3,776,259 | 12/1973 | Kohrumel | 222/83.5 X |
| 3,976,073 | 8/1976 | Quick et al. | 604/414 |
| 4,170,994 | 10/1979 | Komatsu | 604/251 |
| 4,201,208 | 5/1980 | Cambio, Jr. | 604/411 |
| 4,201,406 | 5/1980 | Dennehey et al. | 604/411 X |
| 4,203,443 | 5/1980 | Genese | 604/413 |
| 4,340,052 | 7/1982 | Dennehey et al. | 604/905 X |

*Primary Examiner*—Dalton Truluck
*Assistant Examiner*—Michelle N. Lester
*Attorney, Agent, or Firm*—Hayes, Davis & Soloway

[57] ABSTRACT

An attachment device for inserting and removing the spike for obtaining fluids from a medical fluid bag such as an IV bag or a bag for peritoneal dialysis comprises a base holding the spike positioned to be inserted into the neck of the bag, and opposed toggles pivoting on the base which engage the neck of the bag during insertion and push the neck onto the spike. During removal of the spike the toggles operate an engagement which contacts the end of the neck and pushes the spike out of the neck of the bag. The device has a hand operable slide which affects the motions of the toggles and the toggles have dependent legs ending in the engagement. The attachment device is designed to protect the end of the spike and to prevent contamination.

8 Claims, 5 Drawing Figures

ATTACHMENT DEVICE FOR MEDICAL FLUIDS BAG

INTRODUCTION

It is difficult for even a trained professional with all his faculties intact to spike an IV bag or a bag for peritoneal dialysis without difficulty and without contaminating the spike. Removing the bag from the spike and putting a new one on is even more difficult. This is because the elastic neck or tubing of the bag grips the spike and makes it hard to pull out the spike, particularly after the spike has been in the bag for a couple of hours.

Peritoneal dialysis involves introducing dialyzing solution into the abdominal cavity through a hollow needle. Waste products in the bloodstream make their way through the peritoneum into the solution which is then drained away. By repeated renewals of the solution fairly effective purification of the blood can be achieved. If one takes into consideration that a patient on peritoneal dialysis is usually fairly ill and is many times an older person and emotionally upset, perhaps with diabetes and failing eyesight, one can visualize the problems that an ambulatory patient may have in properly spiking a peritoneal dialysis bag and doing so without contaminating the spike.

In emergencies, such as emergency blood transfusions by ambulance attendants, paramedics, and military corpsman under battle conditions, mistakes can readily be made with consequent contamination and there has been a desideratum for a method of reliably spiking medical fluid bags in these situations where the medic is operating under considerable tension and excitement.

THIS INVENTION

This invention is addressed to the above and other problems of the same nature and proposes an attachment device for facilitating the insertion and removal of a spike into a medical fluids bag such as one containing a dialysis solution, an IV solution, or whole or synthetic blood. The device of the invention, besides mechanically assisting through a lever action afforded by opposing toggles or nippers the insertion and removal of the spike, also serves to guide the fluids bag onto the spike for reliable centering of the spike and can if desired be designed to shield the spike from accidental contamination. The mechanical action afforded by the attachment device of this invention overcomes the binding or gripping effect given by elastic material of the neck of the bag on the spike.

In brief compass, the present invention is an attachment device to insert and remove an access spike into a medical fluids container through the wall or seal at the end of an elongated neck on the container. The attachment device is designed to mate with the neck of the bag, which are standardized in size and shape. The attachment device comprises a base plate having two pivots each of which mounts a pinch or toggle arm. The inner ends of the pinch arm when aligned with the line drawn between the pivots are spaced apart a distance less than the thickness of the neck of the fluid container but in the open or closed position lie apart a distance greater than the thickness of the neck. A hand operable slide serves to actuate the pinch arms through push arms attached to the outer ends of the pinch arm. The inner ends of the pinch arms contain pull arms directed downwardly towards the spike and ending in an engagement or connector that serves to engage the end of the fluid container when the spike is being removed from the bag. The pull arms are spaced apart when the device is in the open position a distance greater than the width of the neck and serve to guide the end of the neck to the spike.

In operation the device, held by its base, is inserted onto the neck of the bag with the slide and the pinch arms in the open position until the spike starts to penetrate the neck. When some resistance is encountered, the hand is then transferred to the slide which operates over the base and pushes the slide forward towards the bag causing the pinch arms to exert their toggle action gripping the neck and pivoting to the closed position, drawing the neck onto the spike while so doing. The spike is then positively held onto and into the bag by the closed position of the pinch arms. The gripping/pulling action of the pinch arms is reversed durig removal of the spike by the hand pulling the slide away from the bag and the pinch arms operate an engagement which contacts the end of the neck forcing it off the spike.

By appropriate design of the lengths of the pinch arms on either side of their pivot points such mechanical advantage or leverage as desired can be achieved.

With very little design difficulty the slide can be so designed that in the closed position of the attachment device a cover attached to the slide can fully encase the top of the spike with the bottom being encompassed by the base and the sides being encompassed by the pull arms. This helps to offset the possibility of accidental contamination.

THE DRAWINGS

DESCRIPTION

Figure 1:
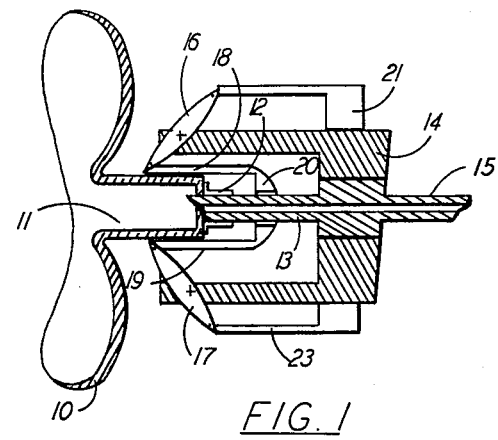
FIG. 1 is a plan sectional view of the attachment device in its open position placed ready to insert the needle thereof into the end wall of the neck of a medical fluids bag.
Figure 2:
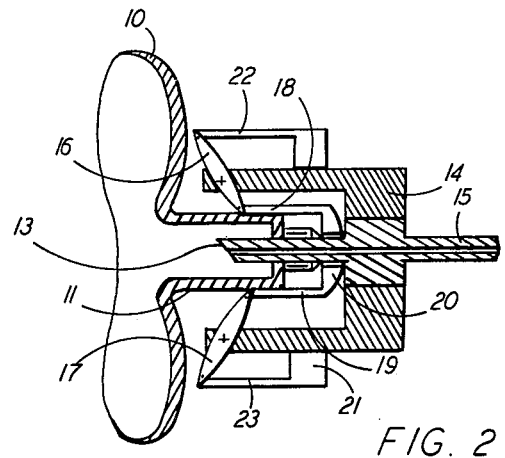
FIG. 2 is a like illustration showing the attachment device in its closed position with the spike fully inserted into the bag.

Referring to FIGS. 1 and 2, a medical fluids bag 10 has a neck 11 ending in a self-sealing penetrable wall 12, as is known. The attachment device shown in section consists of the spike 13 removably mounted to a base 14. The fluid tube 15 running to the patient connects with spike 13.

Toggles 16 and 17 are pivotedly mounted on base 14 with the lengths of the arms on either side of the pivots being sufficient to give about a 2 to 1 mechanical advantage. The space between the inner ends of the toggles when they are at their midpoints on line with the line between the pivots is less than the width of neck 11 whereby when in the mid position they pinch and grab neck 11. The inner ends of toggles 16 and 17 are connected to dependent pull arms 18 and 19 which end in an engagement or connector 20. Connector 20 is open in a center portion to allow the free movement of spike 13 therethrough. Pinch arms 16 and 17, pull arms 18 and 19 and connector 20 are interconnected for articulated movement.

Pinch arms 16 and 17 are actuated by means of a hand operated slide 21 moving back and forth under base 14 which slide has push arm 22 connecting to the outer end of toggle 16 and push arm 23 connecting to the outer end of toggle 17, the arms being connected in a manner to permit articulation.

In operation, the attachment device held primarily by the base 14 is brought while in its open position as shown in FIG. 1 onto the neck 11 of the fluids bag with the inner ends of toggles 16 and 17 and their dependent arms 18 and 19 serving as guides. Neck 11 is inserted until spike 13 commences penetration of the end wall 12 and meets some resistance. At this point the action of the hand is transferred to the slide 21 and slide 21 is pushed toward bag 10 causing toggle 16 and 17 to pivot through their mid position to the closed position and in so doing to pinch and grab the neck of the bag forcing it into the spike as shown in FIG. 2. Preferably the neck of the bag is constructed to engage the ends of toggle 16 and 17 to facilitate the grabbing, pushing action of the toggle. This can be done, for example, by having an enlarged peripheral ring or ridge appriopriately molded into the neck of the bag or by placing serrated depressions on the neck to engage like ridges on the tips of toggles 16 and 17. The necks on most commercial bags have a ring stiffener in them where the sealing membrane is, and the pinch arms can be designed to grab this stiffener to push the neck onto the spike.

With reference to FIG. 2, when the device is in its fully seated closed position, toggles 16 and 17 have moved free of the bag thus permitting unrestricted flow from the bag to the spike.

It is desirable when a sharp pointed spike 13 is used not to have the spike centered precisely on the median line between the two toggles. This is because the sharp end of the spike might engage the inner wall of the neck because of the pinching action of the toggles and enter the wall of the neck puncturing it. This possibility can be overcome by placing spike 13 at a slight angle with respect to the median line between the two toggles with the face of the tip of the spike being closer to the wall on that side. This also helps the neck to better find and center on the spike.

The attachment device and the spike is removed from the bag by reversing the operation. After the spike has been resident in the end wall 12 of the bag for sometime, the tubing tends to grip the spike rather firmly making initial movement difficult. This is overcome with this invention by the toggle action of the attachment device. To remove the attachment device slide 21 in a natural movement is pulled by hand from the position shown in FIG. 2 to the position shown in FIG. 1. This causes toggles 16 and 17 to pivot toward the open position and arms 18 and 19 to bring connector 20 into contact with the face of the neck pushing the neck off the spike, or conversely pushing the spike out from the bag. When during removal the attachment device has reached the position shown in FIG. 1 it can be removed the remainder of the way by simply sliding it off the neck of the bag without difficulty by continued action of the hand pulling on slide 21.

Figure 3:
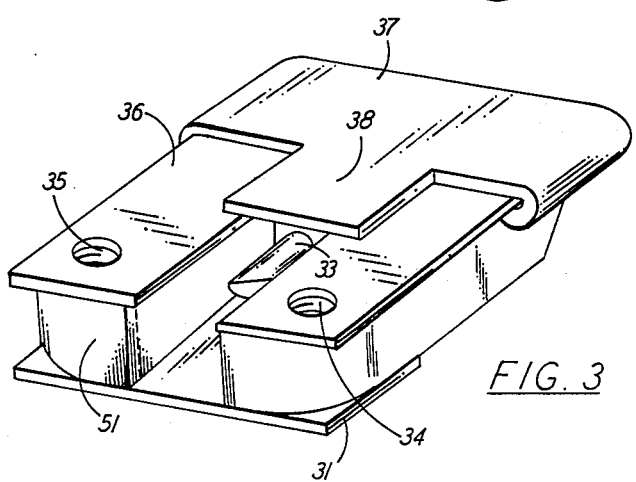
FIG. 3 is a perspective top view of another form of the attachment device.
Figure 4:
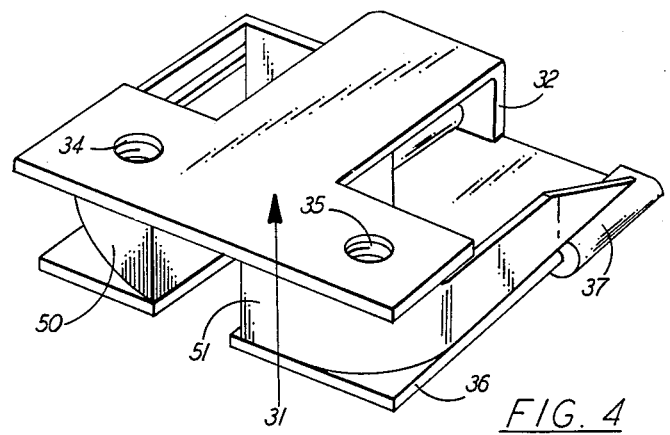
FIG. 4 is a perspective bottom view.
Figure 5:
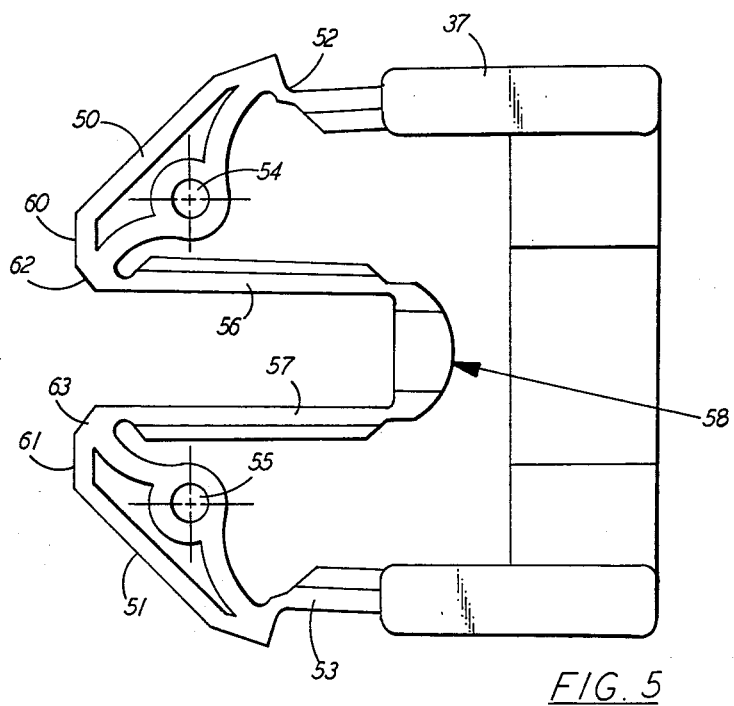
FIG. 5 is a plan view illustrating how the slide, the toggles with their operating arms, and the neck engagement can be integrated into a single molded plastic piece, suitably articulated.

FIGS. 3, 4 and 5 illustrate an embodiment of the device made of molded plastic so as to be inexpensive and disposable. The base 31 is planar and ends in a turned up end wall 32 which serves to engage and hold spike 33. The base carried two pivots 34 and 35. The upper ends of 34 and 35 are used to help retain a top cover 36 which is also secured to end wall 32 of the base. Top cover 36 besides adding rigidity to the structure serves as a guide for hand operated slide 37, the ends of which are turned around to engage the edges of top piece 36. Slide 37 has a tongue 38 that extends over the trough containing spike 33 when the attachment device is in its open position thus serving, along with the base, to protect the spike from contamination.

Mounted for movement between the top piece 36 and base 31 are toggles 50 and 51 articulately connected at the outer ends to push arms 52 and 53 respectively which are in turn attached to slide 37. Toggles 50 and 51 have bores 54 and 55 respectively which are mounted on pivots 34 and 35, respectively. The inner ends of the toggles 50 and 51 are connected by articulated joints to dependent pull arms 56 and 57, respectively, which in turn are articulately connected to an engagement piece or connector 58. Connector 58 has a center opening to permit passage of spike 33.

In this design, the ends of the toggles or nippers 50 or 51, rather than being rounded, have faces on the ends engaging the neck of the fluids bag which enhance the gripping pulling/pushing action of the nippers. Thus arm 50 has faces 16 and 62 and arm 51 has faces 61 and 63. As mentioned previously these faces can be serrated or roughened in some manner to enhance their gripping and holding action.

It can be appreciated that the base 31, the arms 56 and 57, and the slide 37 with its tongue 38 form a trough or guide aiding in the insertion of the neck of the bag and the guiding of it onto the spike. In another version of the attachment device it may be desirable to do away with shield 38 to permit the user to apply an antispetic to the spike before use.

I claim:

1. In combination, a fluid container and a device adapted to insert and remove an access spike from a wall of said container; said container having an elongated neck said wall being disposed at the end of said neck, said device having an open position and a closed position, said device comprising:
   a. a base member;
   b. two pivot members on said base member;
   c. pinch arm elements mounted on each of said pivot members, and adapted to rotate thereabout, each of said pinch arm elements having an inner end and an outer end, the inner ends of the pinch arm elements when aligned with a line drawn between said pivot members being spaced apart a distance less than the diameter of said neck but lying apart a distance greater than said diameter when the device is in its open position;
   d. push arm elements pivotally connected at one end thereof to the outer end of each of said pinch arm elements, said push arm elements being of substantially equal length and movable back and forth on a line generally parallel to the longitudinal axis of said neck;
   e. a hand operable slide member bridging the other ends of said push arm elements;
   f. pull arm elements pivotedly connected at one end thereof to the inner end of each of said pinch arm elements, each of said pull arm elements being of substantially equal length and moveable in the same direction as said push arm elements and generally parallel thereto;

g. a connector member pivotedly connected to the other ends of said pull arm elements and spacing them apart a distance greater than the diameter of said neck;

h. a hollow spike member affixed to said base member and generally aligned with said longitudinal axis, one end of said spike member facing and adapted to penetrate said wall, said spike member being disposed within said connector but being free to move relative thereto; and i. a fluid conduit member affixed to the other end of said spike member;

whereby, when said device is in its open position and said one end of said spike member is adjacent said wall, motion of said slide towards said fluid container causes said pinch arms elements to rotate through a position where the inner ends thereof are in their closest position and into the closed position of the device with the inner ends of said pinch elements engaging said neck during their rotation thereby pulling said base member towards and said spike member into said wall.

2. The combination of claim 1 wherein said pull arm elements and said base member form a guide channel for said neck.

3. The combination of claim 2 wherein said base member is planar and said slide includes a cover attached thereto on the side opposite said base member and covering said spike member when said device is in said closed position.

4. The combination of claim 1 wherein when said spike member is inserted into said wall and said pinch arm elements are moved from the closed to the open position, said connector member is positioned to engage the end of said neck causing said pivot members and base member to move away from said neck and extract said spike member.

5. An attachment device mating with the neck of a liquid container, said neck being elongated and having a predetermined diameter, said neck terminating in a penetrable end wall, said attachment device having an open operating position and a closed operative position, said device comprising:

a. a base member having two pivot members mounted thereon;

b. a nipper member having two spaced arm elements, each said arm element being disposed for pivotal motion about one of said pivot members, each said arm element having an inner end and an outer end, said inner ends having a most open position and a closest position, said inner ends being spaced apart a distance greater than said diameter when in said most open position and being spaced apart a distance less than said diameter when in said closest position so as to engage and squeeze said neck;

c. an engagement tube mounted to said base member substantially on the center line between said arm elements and having a pointed end facing said arm elements, said tube being positioned so as to penetrate said end wall when said attachment device is in said closed operating position;

d. hand operable means for moving said nipper member, the movement thereof causing said arm elements to pivot from said most open position through said closest position thereby causing said arm elements to draw said neck inserted therebetween towards said pointed end of said engagement tube and effecting penetration of said end wall, said movement thereby effecting the movement of said device from said open operating position to said closed operating position; and e. leg elements pivotally attached to the inner end of each of said arm elements and dependent therefrom extending inwardly towards and beyond said pointed end, and a connector member connecting the inward ends of said leg elements, said connector member permitting the movement of said engagement tube therethrough and contacting the end of said neck when said hand operable means moves said nipper member from said closest position towards said most open position and effecting thereby motion of said base member away from said neck and said tube away from said end wall.

6. A connector for a fluid container having a neck of predetermined diameter ending in a penetrable end wall, comprising:

a. a base member;

b. a hollow spike member positioned on said base member and adapted to penetrate the end of said neck as said neck is moved towards said hollow spike member;

c. at least one toggle member adjacent the path of travel of said neck and pivotable inwardly on said base member so that the end of said toggle member moves from a open position away from said spike member to a closed position near said spike member, the end of said toggle member pinching said neck at an intermediate point of arcuate travel and said end of said toggle member pushing said neck at said intermediate point of travel and forcing said neck toward said hollow spike member as said toggle member moves to the closed position thereof;

d. guide means on said base member for directing said neck along its longitudinal axis over said base member, part of said guide means being spaced apart a distance less than said diameter at said intermediate point of acruate travel and including means to retain said neck against lateral motion;

e. a leg member articulately attached at one end thereof to said end of said toggle member, dependent therefrom and extending towards said hollow spike member and an engagement means at the end of said leg member adapted to engage the end of said neck when said neck is seated in the connector and said toggle member is moved from said closed position to the open position thereof; and f. a hand operated means for effecting motion of said toggle member from said closed position to said open position.

7. The connector of claim 6, having a pair of said toggle members opposed one to another and with each toggle member having a said leg member dependent therefrom and connected to said engagement means said toggle members and said leg members serving as said guide means, and wherein said base member is planar and said hand operated means is a slide member operating over and against said base member.

8. The connector of claim 6 wherein said part of said guide means is another toggle member.

* * * * *